United States Patent
Saito

[19]

[11] Patent Number: 5,968,022
[45] Date of Patent: Oct. 19, 1999

[54] MEDICAL HOLLOW NEEDLE AND METHOD OF PRODUCTION

[76] Inventor: Yoshikuni Saito, Ooaza Kitanogami 1930, Kurobanemachi, Nasu-gun, Tochigi-Ken, Japan

[21] Appl. No.: 09/167,870

[22] Filed: Oct. 7, 1998

Related U.S. Application Data

[63] Continuation-in-part of application No. 08/634,343, Apr. 18, 1996, Pat. No. 5,820,609, which is a continuation-in-part of application No. 08/504,038, Jul. 19, 1995, Pat. No. 5,575,780.

[30] Foreign Application Priority Data

| Apr. 28, 1995 | [JP] | Japan | HO7-129297 |
| Jun. 14, 1995 | [JP] | Japan | HO7-17438 |
| Jan. 12, 1996 | [JP] | Japan | HO8-21988 |

[51] Int. Cl.⁶ .................................................. A61M 5/32
[52] U.S. Cl. ..................................... 604/272; 604/264
[58] Field of Search ................................. 604/272, 264, 604/500; 606/167, 222, 223

[56] References Cited

U.S. PATENT DOCUMENTS

| 1,749,919 | 8/1930 | Mierley . |
| 2,751,907 | 9/1956 | Hickey . |
| 3,308,822 | 4/1964 | De Luca . |
| 3,924,617 | 12/1975 | Ferro . |
| 4,368,738 | 1/1983 | Tersteegen et al. . |
| 4,490,139 | 12/1984 | Huizenga et al. . |
| 5,484,422 | 1/1996 | Sloane, Jr. et al. . |
| 5,575,780 | 11/1996 | Saito . |
| 5,788,679 | 8/1998 | Gravlee, Jr. ............................. 604/272 |
| 5,807,317 | 9/1998 | Krech, Jr. ............................ 604/272 X |
| 5,810,788 | 9/1998 | Racz .................................... 604/264 X |
| 5,820,609 | 10/1998 | Saito . |

*Primary Examiner*—John D. Yasko
*Attorney, Agent, or Firm*—Duane, Morris & Heckscher LLP

[57] ABSTRACT

A needle has a hollow cylindrical member defining a lumen along a center axis. A first bevel face is formed at an incline across an end portion of the needle between opposite outer wall surfaces having a first inclined angle with respect to the axis. Second and third bevel faces (i.e., a right bevel face and a left bevel face) converge inwardly from point along the first bevel face to an endmost point where their planes intersect. The right and left bevel faces are formed by relatively rotating the needle through a first rotational angle and grinding the respective converging bevel face. The second and third bevel faces converge at a second more-steeply inclined angle to the point. Opposite from the first bevel face, a sub-bevel face is formed in an oblique direction with respect to the axis center, thinning the wall thickness of the cylindrical member. The point is thus provided with a prow-like cutting edge inclined rearwardly from the point at the intersection between the second and third bevels, and two lateral cutting edges at the intersection of the sub-bevel and the second and third bevels, respectively. The result is a sharp and durable point where the cutting edges converge at a relatively steep angle, the point being spaced radially inwardly from an extension of the outer wall of the cylindrical member.

13 Claims, 4 Drawing Sheets

MEDICAL HOLLOW NEEDLE AND METHOD OF PRODUCTION

CROSS REFERENCE TO RELATED APPLICATION

This is a continuation-in-part application of copending application Ser. No. 08/634,343, filed Apr. 18, 1996, now U.S. Pat. No. 5,820,609, which is a continuation-in-part of Ser. No. 08/504,038, filed Jul. 19, 1995, now U.S. Pat. No. 5,575,780.

BACKGROUND OF THE INVENTION

1. Field of the Invention

This invention relates to a hollow needle suitable for use in medical applications, such as insertion into a blood vessel or other tissue for hypodermic injection, insertion of a cannula for transfusion, dialysis, intravenous drip, blood-collecting and the like, these functions being generally termed "injections" herein. More particularly, a cannular needle defining a flow path in which a fluid such as a liquid medicine or blood can pass in one direction or the other, is provided with a specifically formed point. The invention also concerns the method for producing the needle and the point involving the formation of an oblique planar bevel, a back bevel and two laterally converging bevels, resulting in a sharp end having a prow shape with three cutting edges converging into an end point.

2. Prior Art

The point of a conventional hollow needle, such as a needle intended for hypodermic injection, is formed by selectively grinding an end of a tube or hollow cylinder to form a point. The tube normally has a narrow diameter and advantageously the point is as sharp as practicable, to facilitate the piercing of tissues.

Typically, the end portion of the cylinder is ground along a flat plane extending in an oblique direction relative to the axis of the tube or hollow cylinder, i.e., in a direction that converges with the longitudinal axis of the cylinder at an acute angle, crossing the axis to the opposite outside wall at the extreme end point. Assuming an arbitrary position of the needle wherein the bevel slopes downwardly from a "top" wall of the cylinder to a point at the outer edge of the "bottom," this planar bevel results in an open bevel end-face on a side of the point wherein the lumen is oval in plan view and is surrounded by an elliptical annulus between the lumen, and the top outer wall and the bottom outer wall (namely the point). Without further grinding, the point forms the rounded chord of the minor side of an ellipse at the extreme end.

If the tapering wall thickness of the extreme end of the cylinder is made very thin during manufacturing, the point is very sharp and will inflict less injury to the skin, blood vessel or other tissue at the point of injection of the patient than will a thicker, duller point. To improve sharpness, the acute angle of the oblique bevel forming the point can be a very small angle, making the point very thinly tapered to the extreme end. Consequently, less pain is felt by the patient during the injection. However, if the acute angle of the oblique bevel is made relatively smaller, the axial extension of the elliptical annulus becomes longer between the lumen or inner wall and the extreme end or point at the outer wall. As a result, there is an elongated point have very little thickness or strength of metal at and adjacent to the extreme end or point of the needle due to the axially elongated and thinly tapered bevel end-face. Needles of this type are disclosed, for example, in U.S. Pat. No. 3,308,822—De Luca and International Application No. PCT/NO91/00104 (International Publication WO 92/04062). With extreme tapering and thinness at the point, the metal approaching the tip becomes as thin as a foil, the tip is difficult to grind in a manner that preserves the shape of a smooth ellipse at the tip, may overheat in grinding and is easily bent.

International Application No. PCT/NO91/0104 also discloses the possibility of a back bevel on a needle having an oblique bevel face as described. Assuming as above that the needle is oriented such that the oblique bevel tapers downwardly from a top wall to the point as above, the back bevel tapers upwardly from the bottom wall to the point. A back bevel is advantageous in that the extreme end or point of the needle is moved radially inwardly from the bottom wall. This reduces the possibility of piercing the far wall of a blood vessel during an intravenous injection. However such a back bevel tends to increase the lateral width of the point of the needle as compared to the shape of the minor chord of an ellipse.

There is a need for an improved needle and method for producing it that will provide an extremely sharp edge portion that is thin, but strong at the same time. Preferably, the improved needle should have the point spaced radially inward from an extension of the outer wall, and preferably the back bevel cut to accomplish this should not unduly thin and weaken the strength of the tip approaching the tip.

SUMMARY OF THE INVENTION

A preferred embodiment of the present invention provides a needle adapted for use in medical procedures comprising a tube or hollow cylindrical member having a top end portion and including a fluid flow path along a central axis. A first bevel face is formed at the top end portion such that a flow path opening is defined at an oblique orientation relative to the central axis, thus defining a first inclined angle. A second substantially vertically cut bevel face is formed by rotating the cylindrical member about the central axis and through a first rotational angle while grinding the bevel face so as to define a second steeply inclined angle. A third bevel face is formed by rotating the cylindrical member about the central axis and through a second rotational angle, in an opposite direction with respect to the first rotational angle, while grinding the first bevel face so as to define a third steeply inclined angle. The second and the third bevel faces are formed at the top end portion of the cylindrical member and converge toward a point at the tip. At the intersection of the second and third bevel faces, a forward cutting edge is defined, oriented obliquely to the central axis and the first bevel face, and extending rearwardly from the point at the tip for a short distance, for example approximately equal to the radial thickness of the tube wall. A fourth bevel face is formed as a back bevel in the end portion of the cylindrical member, converging toward the point at an incline opposed to the first bevel face, in an oblique direction with respect to the central axis and the forward cutting edge.

The forward cutting edge along the line of intersection the second and third bevel faces forms a sort of inverted prow leading to an extreme point at the tip. The point is thus formed by the intersection of three bevel faces (the second through fourth). Although the bevels are all at a relative small acute angle relative to the longitudinal axis of the tube, the second through fourth bevels cause the point to converge at a relatively larger acute angle relative to one another at the extreme tip. Thus the point is quite sharp yet also strong, and the point at the extreme end is spaced radially inward from an extension of the tube outer wall.

The present invention also provides a method of producing a needle comprising the steps of grinding a top end portion of a cylindrical member having a fluid flow path along a central axis so as to form a tapered first face wherein the outer diameter of the cylindrical member is reduced toward a top edge by thinning the wall thickness of the cylindrical member. The top end portion of the cylindrical member is then ground to form a first bevel face oriented in an oblique direction, and having a first inclined angle with respect to the central axis wherein the flow path opens in an oblique direction. The top end portion is then ground while rotating the cylindrical member about the central axis, and through a first rotational angle so as to form a second substantially vertical bevel face. Finally, the top end portion is ground while rotating the cylindrical member about the central axis, and through a second rotational angle, in an opposite direction to the first rotational angle so as to form a third, substantially vertical bevel face.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein.

DETAILED DESCRIPTION OF THE PREFERRED EMBODIMENT

Figure 1:
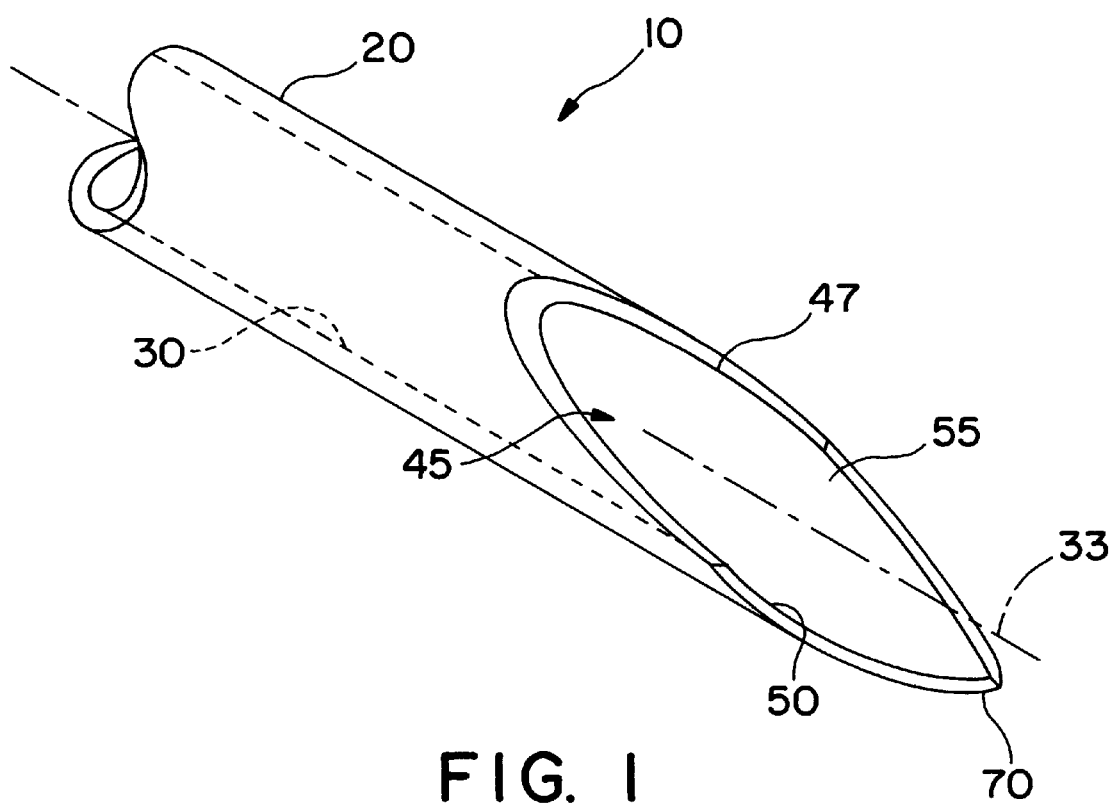
FIG. 1 is a perspective view of a needle formed in accordance with the present invention
Figure 2:
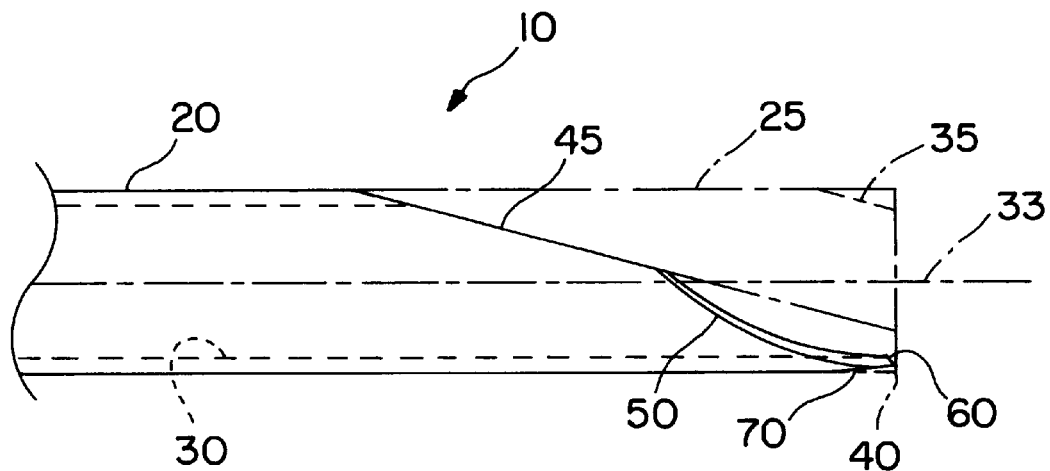
FIG. 2 is a side elevational view, partially in phantom, of the needle shown in FIG. 1.
Figure 3:
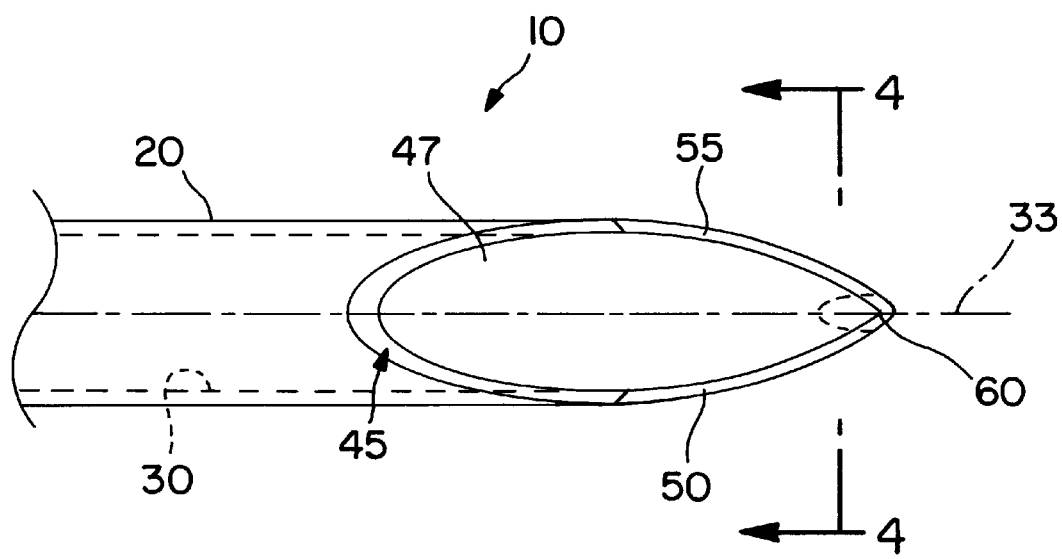
FIG. 3 is a top view of the needle shown in FIG. 1.

The following description of the preferred embodiment of the invention is intended to be read in connection with the foregoing drawings and is to be considered a portion of the entire written description of this invention. As used in this description, terms such as "top," "bottom," "horizonal, " "vertical," "left," "right," "up, " "down," and derivatives thereof refer to the orientation of the structure of the invention as it is illustrated in the particular drawing figure, wherein the invention is shown in an arbitrary and non-limiting orientation. Similarly, the terms "inwardly" and "outwardly" generally refer to the orientation of a surface relative to its axis of elongation, or axis of rotation, as appropriate. The terms "connected" and "interconnected," when used in this disclosure describe the relationship between two or more structures, and means that the structures are secured or attached either directly or indirectly through intervening structures. "Operatively connected" means that the foregoing connection between the structures allows such structures to operate as intended by virtue of such connection.

Referring to FIGS. 1–5, a needle 10 is produced by grinding a cylindrical member 20 having a top end portion 25. Cylindrical member 20 may be made of stainless steel tubing as conventionally used for hypodermic or vascular needle tubes. The tubing can be of any appropriate diameter. Relatively small tubing, e.g., in the range from about 1 to 2 millimeter (mm), is appropriate for intravenous injection, and relatively larger tubing is appropriate for a trocar or other surgical use.

The respective grinding operations required to form needle 10 according to the invention may be carried out on conventional CNC grinding machines of the type well known in the art. Needle 10 defines a central lumen 30 which has a relatively small diameter and extends along a longitudinal axis 33. The grinding operations form a sharp point at the end, and the tubing of the needle extends an indefinite distance to a proximal end (not shown) at which the needle is typically mounted to a base.

The edge 40 of top end portion 25 (shown in phantom in FIG. 2) is provided with a sub- or back-bevel face 35. Sub-bevel face 35 can be formed by taperingly grinding edge 40 so as to reduce the outside diameter of cylindrical member 20 approaching the extreme end. In the embodiment shown, sub-bevel face 35 is circumferentially tapered in a conical manner to about a 2 to 15 degree angle with respect to the outer surface cylindrical member 20 so as to be oriented obliquely with respect to longitudinal axis 33 of cylindrical member 20. Preferably, sub-bevel 35 is tapered to about a 3 degree angle. The end of the tube at edge 40 takes on the shape of a circular truncated cone having an open end with lumen 30 centrally disposed in the narrow end of the truncated cone.

A first or primary bevel face 45 is cut on top end portion 25. First bevel face 45 is formed by cutting or grinding top end portion 25 of cylindrical member 20 at an angle that is inclined or oblique to the longitudinal axis 33. This cut may be at differing acute angles (with respect to longitudinal axis 33) in the range from about 10 to about 25 degrees, the angle being about 17 degrees in the embodiment shown. This results in a first bevel face 45, oriented obliquely to longitudinal axis 33 of cylindrical member 20, extending from one outside wall to the other. The first bevel face forms an oval tube edge 47 (see FIGS. 3 and 4). Typically, oval tube edge 47 defines a major axis of about 5 mm to 7 mm, with about 5.9 mm being preferable.

Second and third, substantially vertically cut bevel faces 50 and 55 are formed in opposite lateral sides of oval tube edge 47. The second bevel face is formed by relatively rotating cylindrical member 20 about longitudinal axis 33 through a first rotational angle 48 while grinding a lower quarter of oval tube edge 47 along a plane that converges laterally inwardly toward the extreme end or point. This operation forms second bevel face 50 at a second inclined angle that is more steeply inclined toward the longitudinal axis 33 than first bevel face 45, namely about 8 to about 45 degrees. The third bevel face 55 is likewise formed in the adjacent lower quarter of oval tube edge 47 of first bevel face 45 by relatively rotating cylindrical member 20 about longitudinal axis 33 through a second rotational angle 49, directed in an opposite sense with respect to the first rotational angle 48, and grinding the opposite inwardly converging bevel 55, which is symmetrical with second bevel 50. This operation forms third bevel face 55 at a third steeply inclined angle of about 8 to about 45 degrees.

Second bevel face 50 and third bevel face 55 intersect at the point or tip of needle 10. The second and third bevel faces intersect along a line having a longitudinal extension due to the fact that they are inwardly inclined and due to the thickness of the tube wall left by a back bevel 70 approaching the point at the extreme tip. Thus, bevels 50, 55 define a forward cutting edge 60 oriented obliquely to longitudinal axis 33 and first bevel face 45. This forward cutting edge is inclined at a substantially steeper angle than the primary bevel 45. Although the ground point as a whole is inclined at a small acute angle taper, the extreme point of the needle is characterized by a steeply tapered point formed by the intersection at the point of second and third bevels 50, 55 and back bevel 35. This forward cutting edge 60 readily penetrates the skin, but due to its specific shape has substantial strength, which prevents the extreme tip from breaking or bending. The point is much more durable than the point of a needle that is flatly bevelled to a tapered point.

Figure 4:
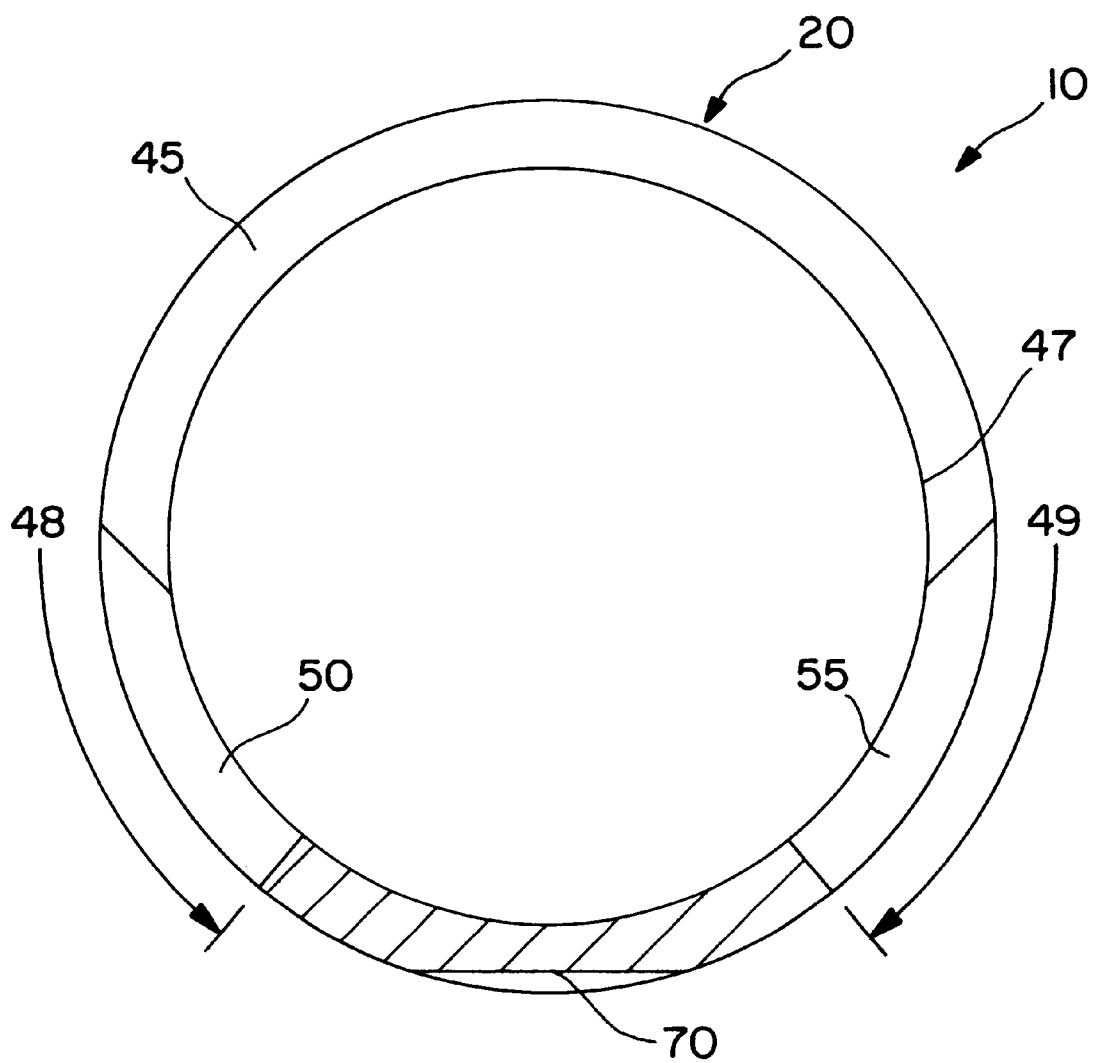
FIG. 4 is a cross-sectional view of the needle shown in FIG. 1, as taken along line 4—4 in FIG. 3.
Figure 5:
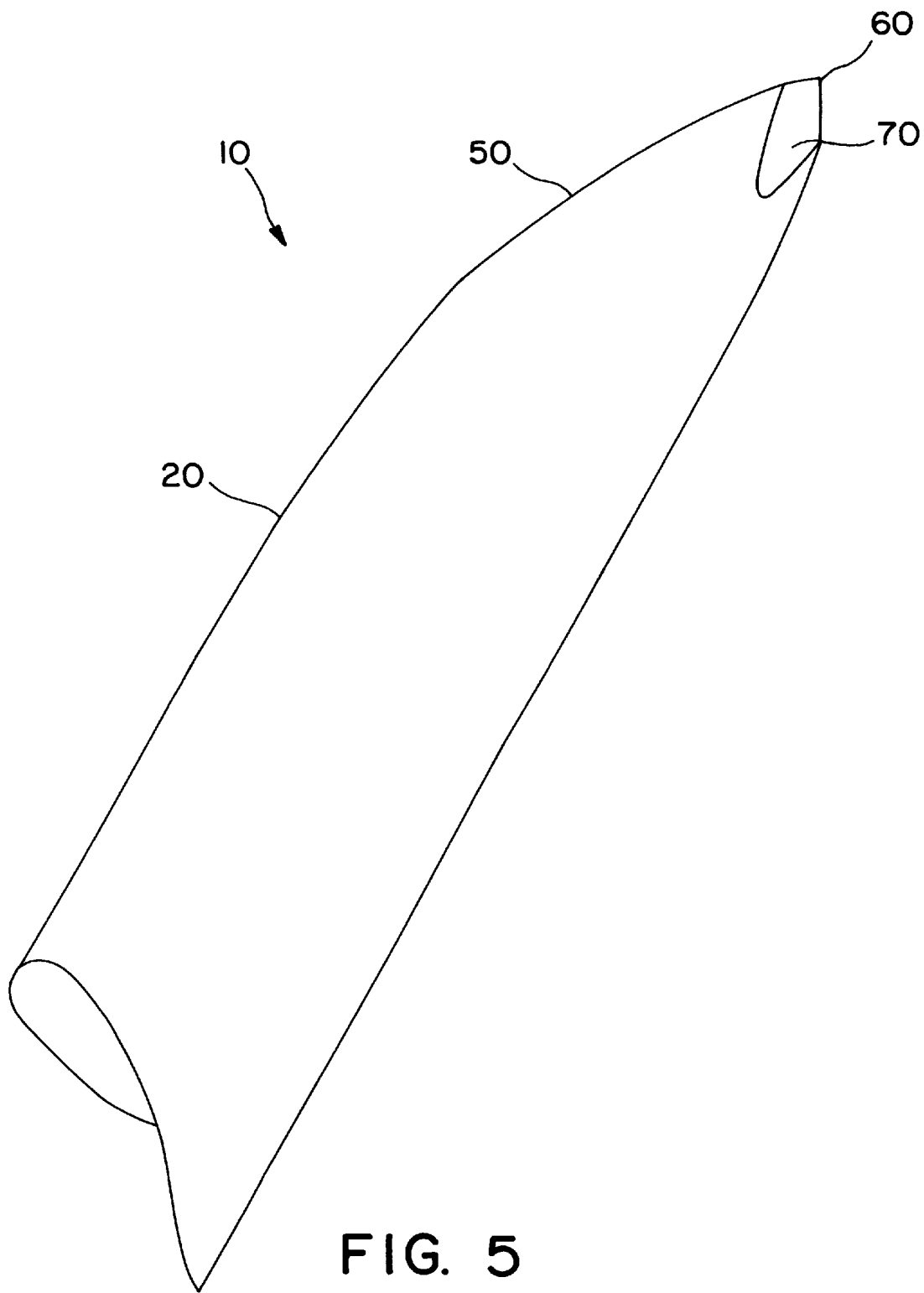
FIG. 5 is a perspective, bottom view of an alternative embodiment of the needle shown in FIG. 1.

According to the foregoing description, due to the conical taper 35 formed in the tube, after grinding of the point, a fourth bevel face 70 is formed in end portion 25 of cylindrical member 20, and bevel face 70 is circumferentially rounded. Alternatively and as best shown in FIGS. 4 and 5, the back bevel can be ground as a flat planar bevel inclined inwardly toward the axis on a side diametrically opposite from first bevel face 45.

In the above description, the needle point is formed by first grinding certain of the bevels (e.g., the primary bevel 45) and then grinding others of the bevels (e.g., second and third bevels 50, 55). The order in which the bevels are formed is not critical; however this order is preferred. The back bevel can be formed preliminarily, which is particularly convenient in the embodiment wherein the back bevel is circumferentially rounded, or after grinding bevels 45, 50, 55, which is convenient in the case of a planar back bevel.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

What is claimed is:

1. A needle adapted for use in medical procedures comprising:
    a cylindrical member having a top end portion and including a fluid flow path along a central axis;
    a first bevel face formed at said top end portion such that a flow path opening is defined at an oblique orientation relative to said central axis thereby defining a first inclined angle;
    a second substantially vertically cut bevel face converging with the central axis, the second bevel face being formed by relatively rotating said cylindrical member about said central axis and through a first rotational angle and grinding said bevel face so as to define a second steeply inclined angle;
    a third bevel face converging with the central axis, the third bevel face being formed by relatively rotating said cylindrical member about said central axis and through a second rotational angle, in an opposite direction with respect to said first rotational angle, and grinding said third bevel face so as to define a third steeply inclined angle, wherein the intersection of said second and said third bevel faces defines between them a forward cutting edge oriented obliquely to said central axis and said first bevel face; and,
    a fourth bevel face is formed in said top end portion of said cylindrical member, at a position opposed to said first bevel face, and in an oblique direction with respect to said central axis and said forward cutting edge.

2. A medical hollow needle comprising:
    a cylindrical member having a flow path capable of passing a fluid therein along a center axis;
    a first ground bevel face formed at a top end portion of said cylindrical member, such that said flow path is open in an oblique direction, having a first inclined angle with respect to said center axis;
    a second ground bevel face formed by rotating said cylindrical member through a first rotational angle, with respect to said center axis, having a second steeply inclined angle, and a third ground bevel face formed by rotating said cylindrical member through a second rotational angle in an opposite direction with respect to said first rotational angle having a third steeply inclined angle, both formed at said top edge portion of said cylindrical member;
    a fourth ground bevel face in a shape of a plane, formed at a position opposed to said first bevel face in an oblique direction with respect to said center axis, thereby thinning said cylindrical member; and
    a sharp forward edge portion formed by the intersection of at least two bevel faces.

3. The needle according to claim 2, wherein said fourth bevel face is formed at an inclined angle 2–15 degrees with respect to said center axis.

4. The needle according to claim 2, wherein said second and said third steeply inclined angles are equal to each other.

5. The needle according to claim 2, wherein said first and said second rotational angles are equal to each other.

6. A method for producing a needle adapted for use in medical procedures comprising the steps of:
    (a) grinding an end portion of a hollow cylindrical member so as to form a first bevel face between opposite outside walls of the cylindrical member, the first bevel face being oriented in an oblique direction relative to a central axis of the cylindrical member and having a first inclined angle with respect to said central axis;
    (b) relatively rotating and grinding said end portion about said central axis, through a first rotational angle so as to form a substantially vertical bevel face converging along a side edge of said first bevel face;
    (c) relatively rotating and grinding said end portion about said central axis, through a second rotational angle, in an opposite direction to said first rotational angle, so as to form a substantially vertical bevel face converging along another side edge of said first bevel face; and,
    (d) tapering the end portion of a cylindrical member along a back bevel inclined inwardly in a direction opposite from the first bevel such that a thickness of the cylindrical member is reduced leading to a point spaced radially inwardly from an extension of an outer wall of the cylindrical member.

7. The method of claim 6, wherein the back bevel is circumferentially rounded.

8. The method of claim 6, wherein the back bevel is planar.

9. The method of claim 6, wherein the back bevel is formed before said grinding to form the first bevel.

10. A method of producing a hypodermic needle, said method comprising:
    grinding a top edge portion of a cylindrical member in an oblique direction relative to a center axis of said member so as to define a flow path capable of passing a fluid therein, and thereby thinning the wall thickness of said cylindrical member, so as to form a first ground bevel face in the shape of a plane;
    grinding a portion opposed to said first bevel face in an oblique direction, at a first inclined angle with respect to said center axis so as to form a second ground bevel face in which said flow path is obliquely open;

grinding said cylindrical member by rotating through a first rotational angle with respect to said axis center, so as to form a third steeply inclined angle with respect to form a third bevel face, and by rotating said cylindrical member through a second rotational angle in an opposite direction with respect to said first rotational angle to form a fourth steeply inclined bevel grinding face; and forming a sharp forward cutting edge portion comprised of at least said second, said third and said fourth bevel faces.

11. The method of producing a needle as set forth in claims 6 or 10, wherein said fourth bevel grinding face is ground with an inclined angle of 2–15 degrees.

12. The method of producing the medical hollow needle as set forth in claims 6 or 10, wherein said second and third inclined angles are equal to each other.

13. The method of producing the medical hollow needle as set forth in claims 6 or 10, wherein said first and said second rotational angles are equal to each other.

* * * * *